United States Patent
Meyer et al.

(10) Patent No.: US 8,512,395 B2
(45) Date of Patent: Aug. 20, 2013

(54) STENT WITH HORSESHOE SHAPED BRIDGES

(75) Inventors: Michael P. Meyer, Richfield, MN (US); Timothy J. Mickley, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 97 days.

(21) Appl. No.: 13/239,098

(22) Filed: Sep. 21, 2011

(65) Prior Publication Data
US 2012/0172972 A1 Jul. 5, 2012

Related U.S. Application Data

(60) Provisional application No. 61/428,489, filed on Dec. 30, 2010.

(51) Int. Cl.
*A61F 2/06* (2013.01)
(52) U.S. Cl.
USPC .......................................... 623/1.16; 623/1.15
(58) Field of Classification Search
USPC ................................................ 623/1.15, 1.16
See application file for complete search history.

(56) References Cited

U.S. PATENT DOCUMENTS

| | | | |
|---|---|---|---|
| 4,214,587 A | 7/1980 | Sakura, Jr. | |
| 4,553,545 A | 11/1985 | Maass et al. | |
| 4,580,568 A | 4/1986 | Gianturco | |
| 4,649,922 A | 3/1987 | Wiktor | |
| 4,655,771 A | 4/1987 | Wallsten | |
| 4,665,918 A | 5/1987 | Garza et al. | |
| 4,681,110 A | 7/1987 | Wiktor | |
| 4,693,721 A | 9/1987 | Ducheyne | |
| 4,733,665 A | 3/1988 | Palmaz | |
| 4,739,762 A | 4/1988 | Palmaz | |

(Continued)

FOREIGN PATENT DOCUMENTS

| | | |
|---|---|---|
| CA | 2248718 | 9/1997 |
| DE | 29702671 | 4/1997 |

(Continued)

OTHER PUBLICATIONS

Beyar et al, "The BeStent; The Parallel-Serial Jang Stents", Handbook of Coronary Stents, Second Edition, 158-171 & 229-234 (1998).

(Continued)

*Primary Examiner* — David Isabella
*Assistant Examiner* — Dinah Baria
(74) *Attorney, Agent, or Firm* — Vidas, Arrett & Steinkraus, P.A.

(57) ABSTRACT

In at least one embodiment, a stent includes an unexpanded configuration, a nominally expanded configuration, and a fully expanded configuration. The stent further includes a plurality of circumferential bands and a plurality of connectors connecting adjacent circumferential bands to one another. Each circumferential band has a plurality of struts interconnected by bridges. Adjacent struts form strut pairs and are connected to one another at a first end or a second end but not both. Each strut pair defines an opening between the struts of the strut pair; the bridges extend into the openings. In the unexpanded configuration, the struts are straight along their length. Also in the unexpanded configuration, the bridges include two adjacent straight segments that are connected by a u-shaped segment, and the straight segments are parallel to one another and to the longitudinal axis of the stent.

18 Claims, 13 Drawing Sheets

(56) References Cited

U.S. PATENT DOCUMENTS

| | | |
|---|---|---|
| 4,760,849 A | 8/1988 | Kropf |
| 4,762,128 A | 8/1988 | Rosenbluth |
| 4,768,507 A | 9/1988 | Fischell et al. |
| 4,776,337 A | 10/1988 | Palmaz |
| 4,787,899 A | 11/1988 | Lazarus |
| 4,795,458 A | 1/1989 | Regan |
| 4,800,882 A | 1/1989 | Gianturco |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,848,343 A | 7/1989 | Wallsten et al. |
| 4,856,516 A | 8/1989 | Hillstead |
| 4,872,874 A | 10/1989 | Taheri |
| 4,877,030 A | 10/1989 | Beck et al. |
| 4,878,906 A | 11/1989 | Lindemann et al. |
| 4,886,062 A | 12/1989 | Wiktor |
| 4,913,141 A | 4/1990 | Hillstead |
| 4,922,905 A | 5/1990 | Strecker |
| 4,950,227 A | 8/1990 | Savin et al. |
| 4,950,258 A | 8/1990 | Kawai et al. |
| 4,994,071 A | 2/1991 | MacGregor |
| 5,015,253 A | 5/1991 | MacGregor |
| 5,019,090 A | 5/1991 | Pinchuk |
| 5,035,706 A | 7/1991 | Giantureo et al. |
| 5,037,392 A | 8/1991 | Hillstead |
| 5,059,211 A | 10/1991 | Stack et al. |
| 5,061,275 A | 10/1991 | Wallsten et al. |
| 5,064,435 A | 11/1991 | Porter |
| 5,091,205 A | 2/1992 | Fan |
| 5,091,211 A | 2/1992 | Richard |
| 5,092,877 A | 3/1992 | Pinchuk |
| 5,102,417 A | 4/1992 | Palmaz |
| 5,104,399 A | 4/1992 | Lazarus |
| 5,104,404 A | 4/1992 | Wolff |
| 5,108,415 A | 4/1992 | Pinchuk et al. |
| 5,108,417 A | 4/1992 | Sawyer |
| 5,122,154 A | 6/1992 | Rhodes |
| 5,133,732 A | 7/1992 | Wiktor |
| 5,135,536 A | 8/1992 | Hillstead |
| 5,139,480 A | 8/1992 | Hickle et al. |
| 5,147,385 A | 9/1992 | Beck et al. |
| 5,147,400 A | 9/1992 | Kaplan et al. |
| 5,158,548 A | 10/1992 | Lau et al. |
| 5,163,952 A | 11/1992 | Froix |
| 5,195,984 A | 3/1993 | Schatz |
| 5,197,978 A | 3/1993 | Hess |
| 5,217,483 A | 6/1993 | Tower |
| 5,226,913 A | 7/1993 | Pinchuk |
| 5,282,823 A | 2/1994 | Schwartz et al. |
| 5,282,824 A | 2/1994 | Gianturco |
| 5,292,331 A | 3/1994 | Boneau |
| 5,304,200 A | 4/1994 | Spaulding |
| 5,344,425 A | 9/1994 | Sawyer |
| 5,354,308 A | 10/1994 | Simon et al. |
| 5,354,309 A | 10/1994 | Schnepp-Pesch et al. |
| 5,356,423 A | 10/1994 | Tihon et al. |
| 5,366,504 A | 11/1994 | Andersen et al. |
| 5,383,892 A | 1/1995 | Cardon et al. |
| 5,389,106 A | 2/1995 | Tower |
| 5,405,377 A | 4/1995 | Cragg |
| 5,411,552 A | 5/1995 | Andersen et al. |
| 5,443,498 A | 8/1995 | Fontaine |
| 5,449,373 A | 9/1995 | Pinchasik et al. |
| 5,522,881 A | 6/1996 | Lentz |
| 5,591,197 A | 1/1997 | Orth et al. |
| 5,609,627 A | 3/1997 | Goicoechea et al. |
| 5,630,829 A | 5/1997 | Lauterjung |
| 5,632,771 A | 5/1997 | Boatman et al. |
| 5,649,952 A | 7/1997 | Lam |
| 5,697,971 A | 12/1997 | Fischell et al. |
| 5,707,386 A | 1/1998 | Schnepp-Pesch et al. |
| 5,716,365 A | 2/1998 | Goicoechea et al. |
| 5,716,393 A | 2/1998 | Lindenberg et al. |
| 5,718,713 A | 2/1998 | Frantzen |
| 5,725,547 A | 3/1998 | Chuter |
| 5,725,572 A | 3/1998 | Lam et al. |
| 5,735,893 A | 4/1998 | Lau et al. |
| 5,741,327 A | 4/1998 | Frantzen |
| 5,755,770 A | 5/1998 | Ravenscroft |
| 5,755,776 A | 5/1998 | Al-Saadon |
| 5,755,781 A | 5/1998 | Jayaraman |
| 5,766,238 A | 6/1998 | Lau et al. |
| 5,776,161 A | 7/1998 | Globerman |
| 5,776,183 A | 7/1998 | Kanesaka et al. |
| 5,800,520 A | 9/1998 | Fogarty et al. |
| 5,800,521 A | 9/1998 | Orth |
| 5,807,404 A | 9/1998 | Richter |
| 5,810,872 A | 9/1998 | Kanesaka et al. |
| 5,814,063 A | 9/1998 | Freitag |
| 5,824,046 A | 10/1998 | Smith et al. |
| 5,824,059 A | 10/1998 | Wijay |
| 5,827,321 A | 10/1998 | Roubin et al. |
| 5,836,966 A | 11/1998 | St. Germain |
| 5,843,168 A | 12/1998 | Dang |
| 5,855,597 A | 1/1999 | Jayaraman |
| 5,855,600 A | 1/1999 | Alt |
| 5,858,556 A | 1/1999 | Eckert et al. |
| 5,861,027 A | 1/1999 | Trapp |
| 5,868,780 A | 2/1999 | Lashinski et al. |
| 5,873,906 A | 2/1999 | Lau et al. |
| 5,876,432 A | 3/1999 | Lau et al. |
| 5,879,381 A | 3/1999 | Moriuchi et al. |
| 5,895,407 A | 4/1999 | Jayaraman |
| 5,911,754 A | 6/1999 | Kanesaka et al. |
| 5,913,895 A | 6/1999 | Burpee et al. |
| 5,922,020 A | 7/1999 | Klein et al. |
| 5,922,021 A | 7/1999 | Jang |
| 5,925,061 A | 7/1999 | Ogi et al. |
| 5,935,162 A | 8/1999 | Dang |
| 5,938,697 A | 8/1999 | Killion et al. |
| 5,948,016 A | 9/1999 | Jang |
| 5,954,743 A | 9/1999 | Jang |
| 5,980,553 A | 11/1999 | Gray et al. |
| 5,984,929 A | 11/1999 | Bashiri et al. |
| 6,001,123 A | 12/1999 | Lau |
| 6,013,854 A | 1/2000 | Moriuchi |
| 6,017,365 A | 1/2000 | Von Oepen |
| 6,022,371 A | 2/2000 | Killion |
| 6,022,374 A | 2/2000 | Imran |
| 6,027,527 A | 2/2000 | Asano et al. |
| 6,042,597 A | 3/2000 | Kveen et al. |
| 6,042,606 A | 3/2000 | Frantzen |
| 6,053,941 A | 4/2000 | Lindenberg et al. |
| 6,056,775 A | 5/2000 | Borghi et al. |
| 6,059,822 A | 5/2000 | Kanesaka et al. |
| 6,068,656 A | 5/2000 | Von Oepen |
| 6,106,548 A | 8/2000 | Roubin et al. |
| 6,113,627 A | 9/2000 | Jang |
| 6,117,165 A | 9/2000 | Becker |
| 6,129,755 A | 10/2000 | Mathis et al. |
| 6,132,460 A | 10/2000 | Thompson |
| 6,132,461 A | 10/2000 | Thompson |
| 6,146,403 A | 11/2000 | St. Germain |
| 6,162,245 A | 12/2000 | Jayaraman |
| 6,168,619 B1 | 1/2001 | Dinh et al. |
| 6,183,506 B1 | 2/2001 | Penn et al. |
| 6,190,403 B1 | 2/2001 | Fischell et al. |
| 6,190,406 B1 | 2/2001 | Duerig et al. |
| 6,193,747 B1 | 2/2001 | Von Oepen |
| 6,203,569 B1 | 3/2001 | Wijay |
| 6,206,911 B1 * | 3/2001 | Milo ............................ 623/1.15 |
| 6,210,429 B1 | 4/2001 | Vardi et al. |
| 6,221,099 B1 | 4/2001 | Andersen et al. |
| 6,231,598 B1 | 5/2001 | Berry et al. |
| 6,245,101 B1 | 6/2001 | Drasler et al. |
| 6,261,319 B1 | 7/2001 | Kveen et al. |
| 6,264,685 B1 | 7/2001 | Ahari |
| 6,287,331 B1 | 9/2001 | Heath |
| 6,287,336 B1 | 9/2001 | Globerman et al. |
| 6,290,721 B1 | 9/2001 | Heath |
| 6,293,966 B1 | 9/2001 | Frantzen |
| 6,299,635 B1 | 10/2001 | Frantzen |
| 6,309,414 B1 | 10/2001 | Rolando et al. |
| 6,312,459 B1 | 11/2001 | Huang et al. |

| | | |
|---|---|---|
| 6,315,791 B1 | 11/2001 | Gingras et al. |
| 6,325,825 B1 | 12/2001 | Kula et al. |
| 6,325,826 B1 | 12/2001 | Vardi et al. |
| 6,327,772 B1 | 12/2001 | Zadno-Azizi et al. |
| 6,330,884 B1 | 12/2001 | Kim |
| 6,331,188 B1 | 12/2001 | Lau et al. |
| 6,331,189 B1 | 12/2001 | Wolinsky et al. |
| 6,331,190 B1 | 12/2001 | Shokoohi et al. |
| 6,334,871 B1 | 1/2002 | Dor et al. |
| 6,336,937 B1 | 1/2002 | Vonesh et al. |
| 6,340,366 B2 | 1/2002 | Wijay |
| 6,340,367 B1 | 1/2002 | Stinson et al. |
| 6,348,065 B1 | 2/2002 | Brown et al. |
| 6,355,057 B1 | 3/2002 | DeMarais et al. |
| 6,355,058 B1 | 3/2002 | Pacetti et al. |
| 6,358,274 B1 | 3/2002 | Thompson |
| 6,361,557 B1 | 3/2002 | Gittings et al. |
| 6,379,381 B1 | 4/2002 | Hossainy et al. |
| 6,395,020 B1 | 5/2002 | Ley et al. |
| 6,402,777 B1 | 6/2002 | Globerman et al. |
| 6,423,090 B1 | 7/2002 | Hancock |
| 6,461,380 B1 | 10/2002 | Cox |
| 6,471,720 B1 | 10/2002 | Ehr et al. |
| 6,488,703 B1 | 12/2002 | Kveen et al. |
| 6,520,987 B1 | 2/2003 | Plante |
| 6,524,335 B1 | 2/2003 | Hartley et al. |
| 6,524,336 B1 | 2/2003 | Papazolgou et al. |
| 6,533,808 B1 | 3/2003 | Thompson |
| 6,540,775 B1 | 4/2003 | Fischell et al. |
| 6,540,777 B2 | 4/2003 | Stenzel |
| 6,551,351 B2 | 4/2003 | Smith et al. |
| 6,558,415 B2 | 5/2003 | Thompson |
| 6,602,282 B1 | 8/2003 | Yan |
| 6,610,086 B1 | 8/2003 | Kock et al. |
| 6,613,081 B2 | 9/2003 | Kim et al. |
| 6,629,994 B2 | 10/2003 | Gomez et al. |
| 6,652,579 B1 | 11/2003 | Cox et al. |
| 6,656,215 B1 | 12/2003 | Yanez et al. |
| 6,663,664 B1 | 12/2003 | Pacetti |
| 6,706,062 B2 | 3/2004 | Vardi et al. |
| 6,730,116 B1 * | 5/2004 | Wolinsky et al. ............ 623/1.16 |
| 6,730,117 B1 | 5/2004 | Tseng et al. |
| 6,776,793 B2 | 8/2004 | Brown et al. |
| 6,818,014 B2 | 11/2004 | Brown et al. |
| 6,821,292 B2 | 11/2004 | Pazienza et al. |
| 6,846,323 B2 | 1/2005 | Yip et al. |
| 6,854,172 B2 | 2/2005 | Kaese et al. |
| 6,878,162 B2 | 4/2005 | Bales et al. |
| 6,962,603 B1 | 11/2005 | Brown et al. |
| 6,969,402 B2 | 11/2005 | Bales et al. |
| 6,981,986 B1 | 1/2006 | Brown et al. |
| 7,014,654 B2 | 3/2006 | Welsh et al. |
| 7,204,848 B1 | 4/2007 | Brown et al. |
| 7,223,283 B2 | 5/2007 | Chouinard |
| 7,243,408 B2 | 7/2007 | Vietmeier |
| 7,329,277 B2 | 2/2008 | Addonizio et al. |
| 7,331,986 B2 | 2/2008 | Brown et al. |
| 7,354,450 B2 | 4/2008 | Bicek et al. |
| 7,404,823 B2 * | 7/2008 | Gregorich et al. ........... 623/1.15 |
| 7,534,257 B2 | 5/2009 | Richter |
| 7,842,080 B2 | 11/2010 | Chouinard |
| 7,988,717 B2 | 8/2011 | Brown et al. |
| 2001/0029397 A1 | 10/2001 | Thompson |
| 2001/0039447 A1 | 11/2001 | Pinchasik et al. |
| 2001/0044652 A1 | 11/2001 | Moore |
| 2001/0056298 A1 | 12/2001 | Brown et al. |
| 2002/0007212 A1 | 1/2002 | Brown et al. |
| 2002/0022876 A1 | 2/2002 | Richter et al. |
| 2002/0055770 A1 | 5/2002 | Doran et al. |
| 2002/0095208 A1 | 7/2002 | Gregorich et al. |
| 2002/0107562 A1 | 8/2002 | Hart et al. |
| 2002/0111669 A1 | 8/2002 | Pazienza et al. |
| 2002/0116049 A1 | 8/2002 | Girton et al. |
| 2002/0120322 A1 | 8/2002 | Thompson et al. |
| 2002/0123797 A1 | 9/2002 | Majercak |
| 2002/0177893 A1 | 11/2002 | Brown et al. |
| 2003/0004567 A1 | 1/2003 | Boyle et al. |
| 2003/0018380 A1 | 1/2003 | Craig et al. |
| 2003/0055485 A1 | 3/2003 | Lee et al. |
| 2003/0176914 A1 | 9/2003 | Rabkin et al. |
| 2003/0195606 A1 | 10/2003 | Davidson et al. |
| 2003/0225448 A1 | 12/2003 | Gerberding |
| 2004/0002753 A1 | 1/2004 | Burgermeister et al. |
| 2004/0034402 A1 | 2/2004 | Bales et al. |
| 2004/0044401 A1 | 3/2004 | Bales et al. |
| 2004/0073291 A1 | 4/2004 | Brown et al. |
| 2004/0088039 A1 | 5/2004 | Lee et al. |
| 2004/0111147 A1 | 6/2004 | Rabkin et al. |
| 2004/0117002 A1 | 6/2004 | Girton et al. |
| 2004/0143318 A1 | 7/2004 | Tseng et al. |
| 2004/0204751 A1 | 10/2004 | Fischell et al. |
| 2005/0060025 A1 | 3/2005 | Mackiewicz et al. |
| 2005/0125051 A1 * | 6/2005 | Eidenschink et al. ....... 623/1.12 |
| 2006/0052864 A1 | 3/2006 | Harder et al. |
| 2006/0271159 A1 | 11/2006 | Gregorich et al. |
| 2007/0150048 A1 | 6/2007 | Tischler |
| 2007/0219624 A1 | 9/2007 | Brown et al. |
| 2008/0097579 A1 | 4/2008 | Shanley et al. |
| 2008/0221661 A1 | 9/2008 | Bidne et al. |
| 2009/0163994 A1 | 6/2009 | Quigley et al. |
| 2010/0100166 A1 | 4/2010 | Richter et al. |
| 2012/0226342 A1 | 9/2012 | Mickley |
| 2012/0226346 A1 | 9/2012 | Boismier et al. |

FOREIGN PATENT DOCUMENTS

| | | |
|---|---|---|
| DE | 29701758 | 5/1997 |
| DE | 29708689 | 7/1997 |
| DE | 29708879 | 7/1997 |
| DE | 29716476 | 12/1997 |
| DE | 29816878 | 12/1998 |
| EP | 0364787 | 4/1990 |
| EP | 0540290 | 5/1993 |
| EP | 0541443 | 5/1993 |
| EP | 0606165 | 7/1994 |
| EP | 0679372 | 11/1995 |
| EP | 0796597 | 9/1997 |
| EP | 0800801 | 10/1997 |
| EP | 0801933 | 10/1997 |
| EP | 0821920 | 2/1998 |
| EP | 0876806 | 11/1998 |
| EP | 0897698 | 2/1999 |
| EP | 0970664 | 1/2000 |
| EP | 0983753 | 3/2000 |
| EP | 1034751 | 9/2000 |
| EP | 1159934 | 12/2001 |
| EP | 1190685 | 3/2002 |
| EP | 1362564 | 11/2003 |
| JP | 6181993 | 7/1994 |
| WO | 9417754 | 8/1994 |
| WO | 9621404 | 7/1996 |
| WO | 9626689 | 9/1996 |
| WO | 9628116 | 9/1996 |
| WO | 9704721 | 2/1997 |
| WO | 9714375 | 4/1997 |
| WO | 9725937 | 7/1997 |
| WO | 9732543 | 9/1997 |
| WO | 9732544 | 9/1997 |
| WO | 9733534 | 9/1997 |
| WO | 9740780 | 11/1997 |
| WO | 9740781 | 11/1997 |
| WO | 9740782 | 11/1997 |
| WO | 9740783 | 11/1997 |
| WO | 9740784 | 11/1997 |
| WO | 9745073 | 12/1997 |
| WO | 9820810 | 5/1998 |
| WO | 98/26732 | 6/1998 |
| WO | 9837833 | 9/1998 |
| WO | 9847447 | 10/1998 |
| WO | 9925273 | 5/1999 |
| WO | 9944535 | 9/1999 |
| WO | 0030563 | 6/2000 |
| WO | 0132099 | 5/2001 |
| WO | 0158386 | 8/2001 |
| WO | 02060344 | 8/2002 |
| WO | 2004032802 | 4/2004 |
| WO | 2008005535 | 1/2008 |

OTHER PUBLICATIONS

Beyar et al "Newer Stents: Materials and Designs" IAGS Proceedings 9(5): 363-371 (Jun. 1997).

Brochure Entitled Ave Micro Stent TM, Instructions for Use, by Applied Vascular Engineering, Inc., pp. 1-15.

Brochure Entitled "Micro Stent TM", by Applied Vascular Engineering, Inc.

Brochure from Cook Incorporated regarding Gianturco-Rosch Biliary Z-Stents TM, 1989.

Expandable Biliary Endoprosthesis: An Experimental Study, by Carrasco et al., AJR vol. 145, Dec. 1985, pp. 1279-1282.

Self-Expanding Stainless Street Biliary Stents, by Harold G. Coons, MD, Radiology 1989, vol. 170, No. 3 part 2, pp. 979-983.

Gianturco Expandable Metallic Biliary Stents: Results of a European Clinical Trial, by Irving, et al Interventional Radiology, vol. 172, No. 2, Aug. 1989, pp. 321-326.

Japanese Infringements Search on Articulated Expandable Stents, dated Jul. 12, 1995.

Improved Dilation Catheter Balloons, by Stanley B. Levy PhD., Journal of Clinical Engineering, vol. 11, No. 4, Jul.-Aug. 1986, pp. 291-296.

Melzer, A. et al., Performance Improvement of Surgical Instrumental Through the Use of Ni-Ti Materials, Proceedings of SMST-94 The First International conference on Shape Memory and Superelastic Technologies, pp. 401-409 (Mar. 7-10, 1994).

Roguin et al Acute and 30-Day Results of the Serpentine Balloon Expandable Stent Implantation in Simple and Complex Coronary Arterial Narrowing\, The American Journal of Cardiology, 80: 1155-1162 (Nov. 1997).

Roguin et al, "BeStent—the serpentine balloon expandable stent; review of mechanical properties and clinical experience", Artificial Organs, 22(3):243-249 (Mar. 1998).

A View of Vascular Stents, by Richard A. Schatz, MD, From the Arizona Heart Institute Foundation, Phoenix, Arizona, Circulation: vol. 79, No. 2, Feb. 1989, pp. 445-457.

The Self-Expanding Mesh Stent, by Ulrich Sigwart, Section IV Chapter 29, pp. 605-609.

Smart (TM) Stent Brochure(s), Cordis, Johnson & Johnson company.

Starck, E., "First Clinical Experience with the Memotherm Vascular Stent", STENTS State of the Art Future Development, pp. 59-62 (Jun. 1995).

Technical Note Entitled Modifications of Gianturco Expandable Wire Stents, by Barry T. Uchida et al., AJR, vol. 150, May 1988, pp. 1185-1188.

Tracheobronchial Tree: Expandable Metallic Stents Used in Experimental and Clinical Applications, Work in Progress, by Wallace et al, Radiology, Feb. 1986, pp. 309-312.

U.S. Appl. No. 60/076,946, filed Mar. 5, 1998, Tseng et al.

International Search Report and Written Opinion, PCT/US2011/052622, mailed Dec. 6, 2011.

\* cited by examiner

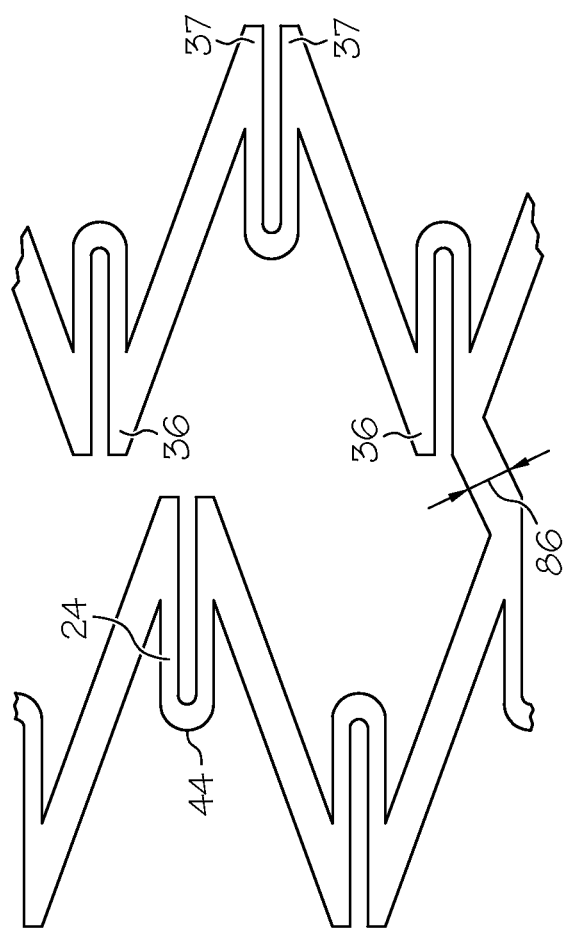

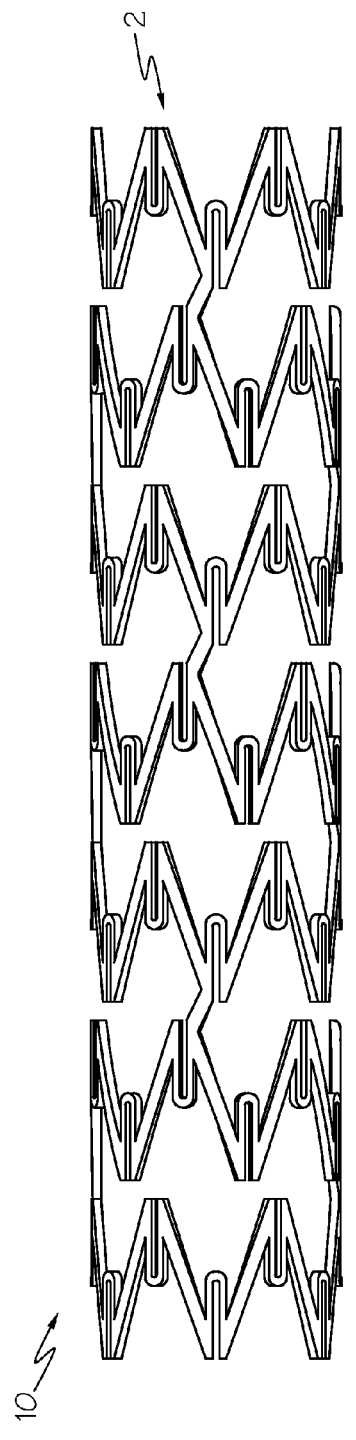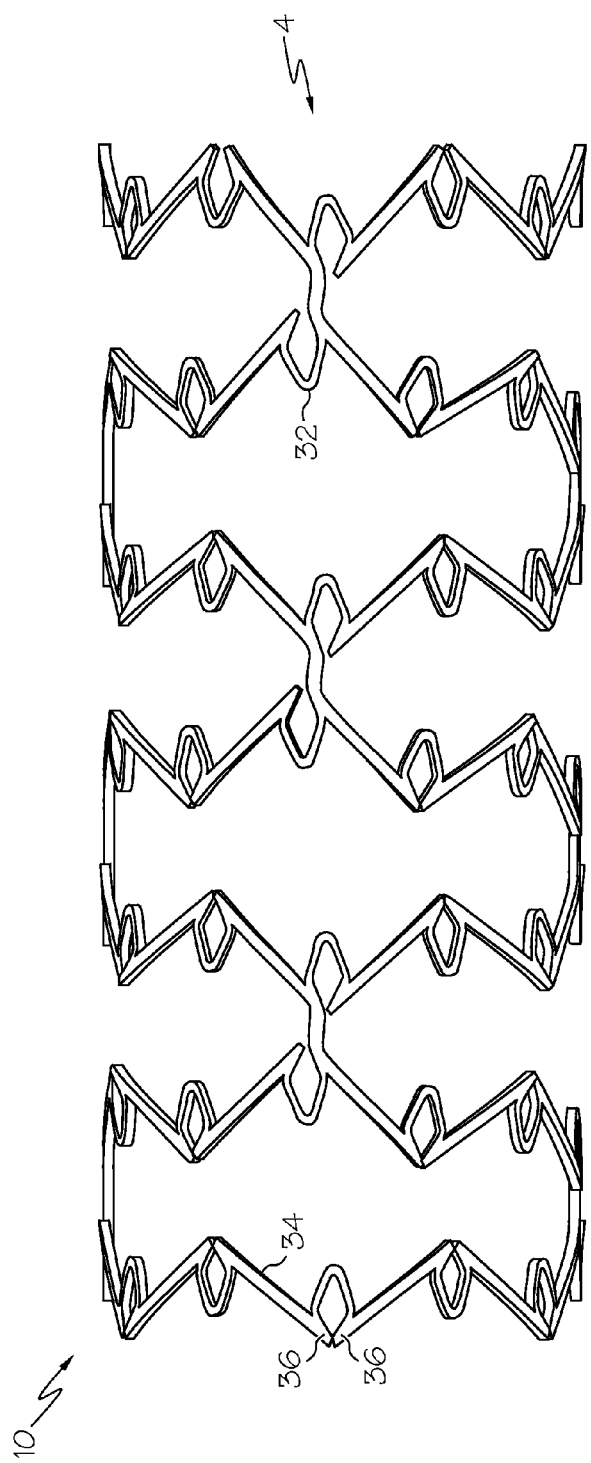

STENT WITH HORSESHOE SHAPED BRIDGES

CROSS-REFERENCE TO RELATED APPLICATIONS

This Application claims priority to U.S. Application No. 61/428,489, filed on Dec. 30, 2010, the entire contents of which are hereby incorporated by reference.

STATEMENT REGARDING FEDERALLY SPONSORED RESEARCH

Not Applicable

BACKGROUND OF THE INVENTION

This invention relates to a stent for insertion into a body lumen or cavity, and more particularly to a stent having the ability to expand in multiple stages.

A stent is a medical device introduced to a body lumen and is well known in the art. Typically, a stent is implanted in a blood vessel at the site of a stenosis or aneurysm endoluminally, by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

There remains a need for novel stent designs that provide benefits over prior designs.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises an unexpanded configuration, a nominally expanded configuration, and a fully expanded configuration. The stent further comprises a plurality of circumferential bands and a plurality of connectors. In the unexpanded configuration, each circumferential band comprises a plurality of circumferentially adjacent strut pairs and a plurality of bridges. Each strut pair comprises a first strut and a second strut. The first strut and the second strut are joined to one another by one of the bridges and the first strut is angularly offset from the second strut by an acute angle when the stent is in the unexpanded configuration. Each bridge comprises two straight segments connected to one another by a u-shaped segment. The two straight segments are parallel to one another and angularly offset relative to the first and second struts, when the stent is in the unexpanded configuration. Circumferentially adjacent strut pairs are connected to one another by one of the bridges. Longitudinally adjacent circumferential bands are connected to one another by at least one of the connectors. And, the first and second struts are wider than the straight segments and the bridges of longitudinally adjacent circumferential bands are circumferentially offset from one another.

In at least one embodiment, a stent comprises an unexpanded configuration, a nominally expanded configuration, and a fully expanded configuration. The stent further comprises a plurality of circumferential bands and a plurality of connectors that connect adjacent circumferential bands to one another. Each circumferential band comprises a plurality of struts and the struts are interconnected by bridges. Adjacent struts form strut pairs and are connected to one another at a first end or a second end but not both. Each strut pair defines an opening with one of the bridges extending into the opening. In the unexpanded configuration, the struts are straight along their length. Also in the unexpanded configuration, the bridges comprise two adjacent straight segments that are connected by a u-shaped segment, and the straight segments are parallel to one another and to the longitudinal axis of the stent.

These and other embodiments which characterize the invention are pointed out with particularity in the claims annexed hereto and forming a part hereof. However, for a better understanding of the invention, its advantages and objectives obtained by its use, reference can be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

FIG. 1B detailed view of the stent of FIG. 1A.

FIG. 1C is a side view showing ½ of the stent of FIG. 1A in an unexpanded configuration.

FIG. 1D is a side view showing ½ of the stent of FIG. 1A in a nominally expanded configuration.

DETAILED DESCRIPTION OF THE INVENTION

Figure 1A:
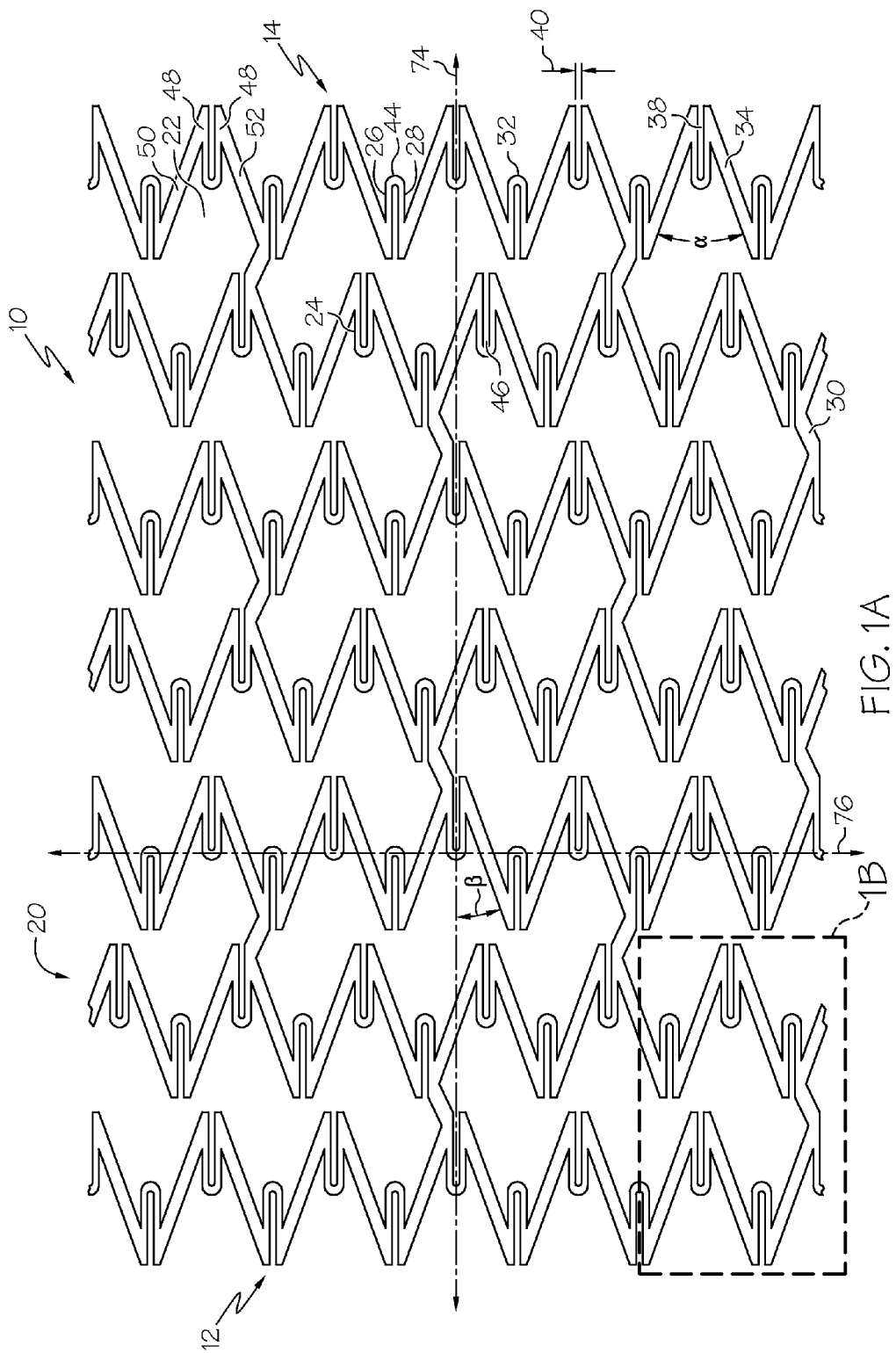
FIG. 1A is flat view of a stent 10.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1E:
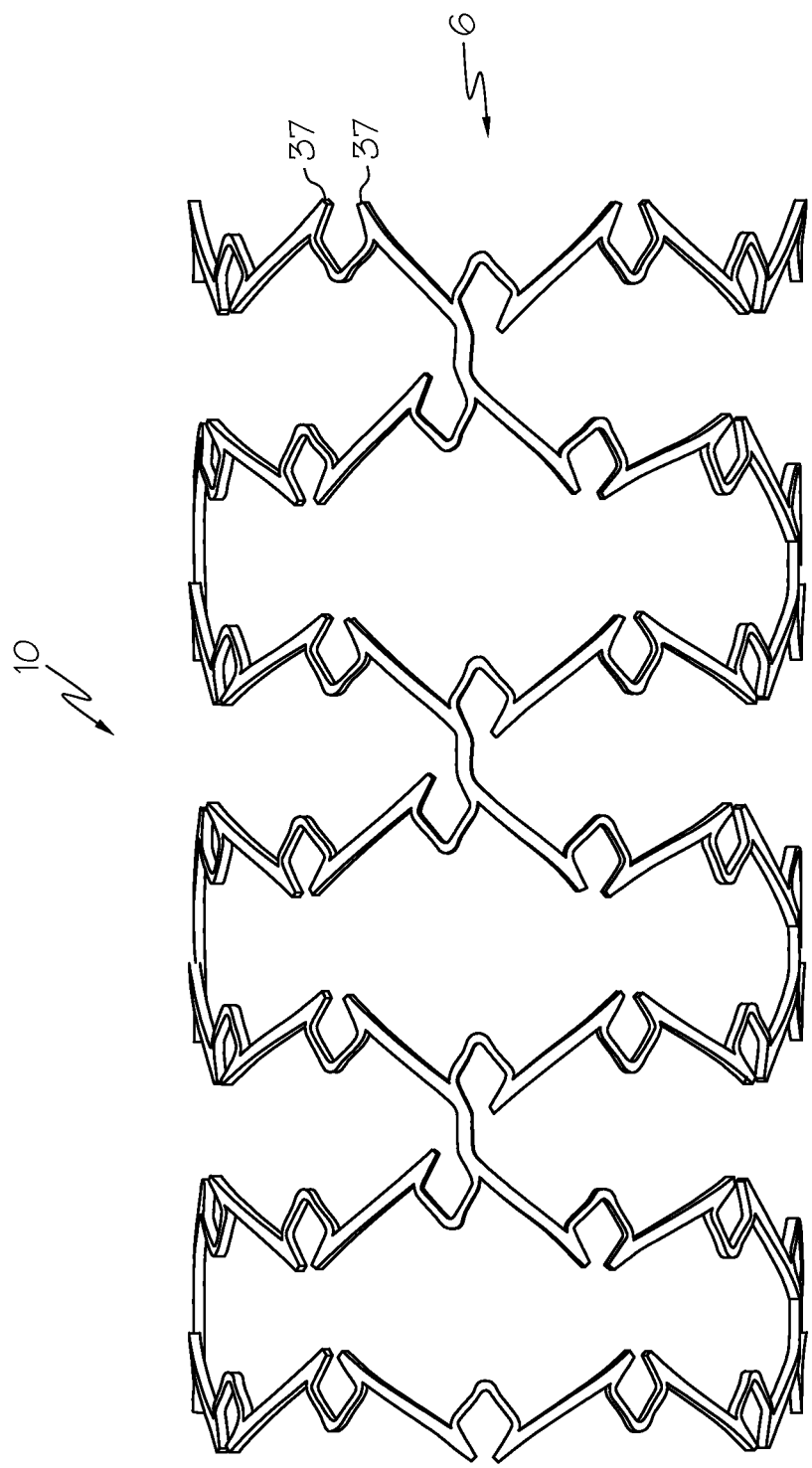
FIG. 1E is a side view showing ½ of the stent of FIG. 1A in a fully expanded configuration.

In at least one embodiment, for example as shown in FIG. 1A, a stent 10 comprises a proximal end 12 and a distal end 14. The stent 10 has an unexpanded configuration 2 (FIG. 1C), a nominally expanded configuration 4 (FIG. 1D), and a fully expanded configuration 6 (FIG. 1E). The stent 10 comprises a plurality of circumferential bands 20 that extend circumferentially around and form the stent wall. In some embodiments, the circumferential bands 20 comprise a closed structure having a tubular shape. In some embodiments, the stent 10 further comprises at least one connector 30, connecting longitudinally adjacent circumferential bands 20. Moreover, the bands 20 comprise a plurality of struts 34 and bridges 32. The bridges 32 connect circumferentially adjacent struts 34 one to another. As shown in FIG. 1B, the struts 34 have a first end 36 and a second strut end 37.

In some embodiments, the circumferential bands 20 comprise a plurality of strut pairs 48, and the strut pairs 48 comprise a first strut 50 and a second strut 52. The first and second struts 50, 52 are attached to one another by a bridge 32. In some embodiments, the first strut 50 and the second strut 52 are separated by an angle α when the stent 10 is in the unexpanded configuration 2, for example as shown in FIG. 1A. In some embodiments, the first and second struts 50, 52 are angularly offset relative to the longitudinal axis 74 by an angle β. In at least some embodiments, angle α=2*β. When the stent is expanded, however, in some embodiments, angle α is right or obtuse.

In some embodiments, at least one of the bridges 32 comprises two straight segments 24, the two straight segments 24 including a first straight segment 26 and a second straight segment 28. The first and second straight segments 26, 28 are circumferentially offset from one another and connected to one another by a u-shaped segment 44. In some embodiments, when the stent 10 is in the unexpanded configuration 2, the straight segments 24 are parallel to one another. In addition, in some embodiments, the straight segments 24 are parallel to the longitudinal axis 74. The first straight segment 26 is separated from the adjacent second straight segment 28 by a gap 38 having a width 40. Moreover, in some embodiments, the u-shaped segment 44 defines a concavity 46. And, in some embodiments, the bridges 32 of every other band 20 lie along a common line of longitude, for example as shown by the longitudinal axis 74 in FIG. 1A.

Circumferentially adjacent first and second struts 50, 52 of a strut pair 48 define an opening 22 therebetween. The opening 22 is bounded on one side by a first strut 50 and on another side by a second strut 52. In some embodiments, for example as shown in FIGS. 1A-1E, the bridges 32 extend into the openings 22.

In some embodiments, the circumferential bands 20 are bisected by a neutral axis 76. In some embodiments, the neutral axis 76 is perpendicular to the longitudinal axis 74.

Turning now to FIG. 1D, the stent 10 is shown in a nominally expanded configuration 4. In the nominally expanded configuration 4, the stent 10 has been expanded from the unexpanded configuration 2 and the bridges 32 have been deformed. In the nominally expanded configuration 4, the bridges 32 flex, while the struts 34 of the strut pairs 48 remain generally straight.

As shown in FIGS. 1D, in some embodiments, circumferentially adjacent ends 36, 36 of adjacent struts 34 of a respective strut pair are closer together when the stent 10 is in the nominally expanded configuration 4 than when in the unexpanded configuration 2. Moreover, in some embodiments, adjacent ends 36, 36 of circumferentially adjacent struts 34 can come into contact with one another in the nominally expanded configuration 4.

In some embodiments, the width of the struts 34 is greater than the width of the straight segments 24 and the width of the u-shaped segment 44, for example as shown in FIG. 1B. The relative widths of the struts 34 and one or more portions of the bridges 32 permits the stent 10 to deform along the bridges 32 prior to any substantial deformation along the length of the struts 34 as the stent 10 is expanded. In some embodiments, the width of the connectors 30 is the same as the width of the straight segments 24.

Turning now to FIG. 1E, the stent 10 is shown in a fully expanded configuration 6. In the fully expanded configuration 6, the stent 10 has been radially enlarged from the nominally expanded configuration 4. In some embodiments, when the stent 10 is expanded to the fully expanded configuration 6, the adjacent ends 37, 37 of circumferentially adjacent struts 34 are separated from one another. In some embodiments, in the fully expanded configuration 6, the adjacent ends 37, 37 of the circumferentially adjacent struts 34 are separated from one another more than when the stent 10 is in the unexpanded configuration 2 and the nominally expanded configuration 4. In addition, in some embodiments, when the stent 10 is expanded to the fully expanded configuration 6, the struts 34 are no longer straight. Instead, in some embodiments, the struts 34 are deformed.

Figure 2A:
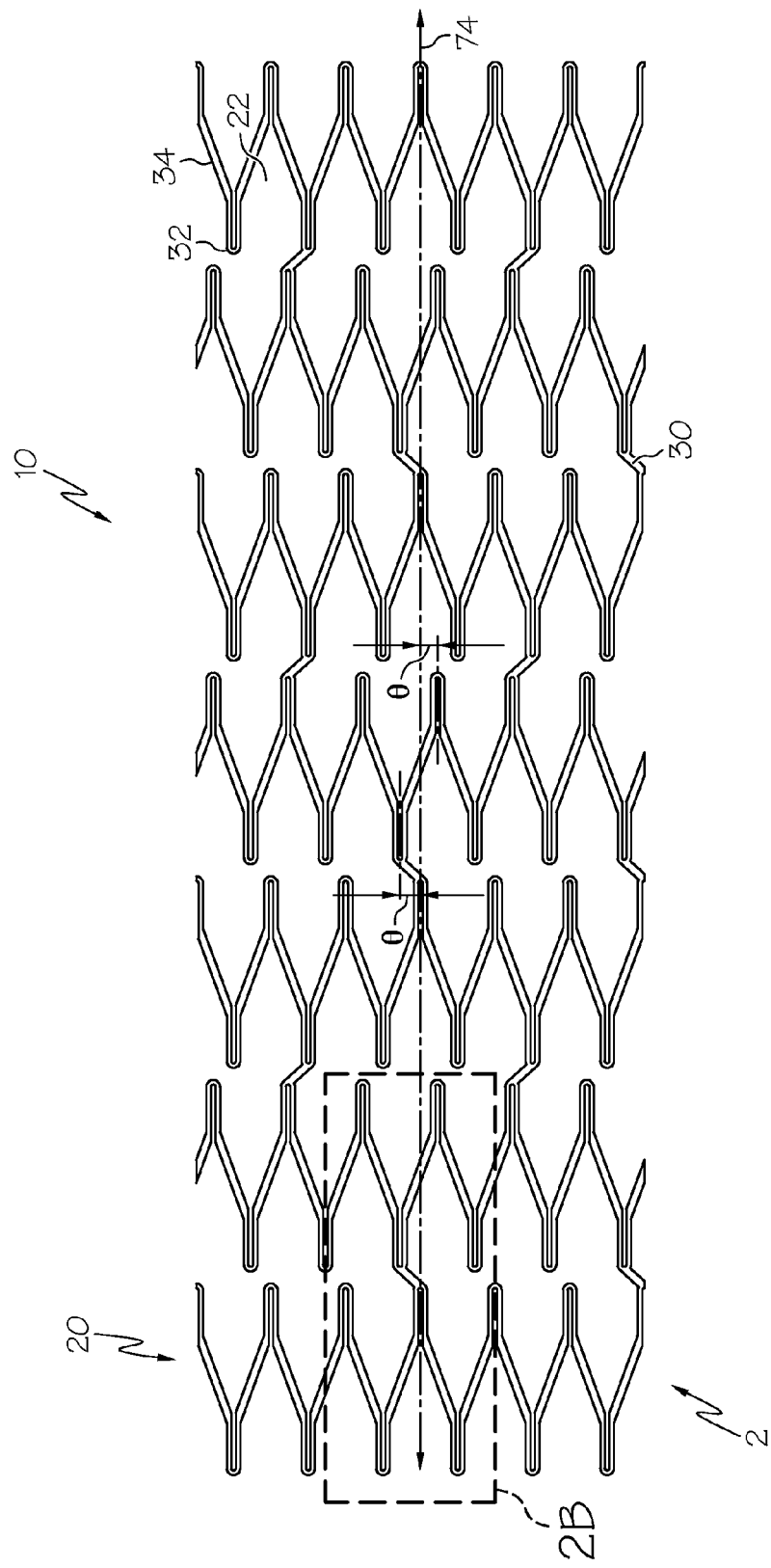
FIG. 2A is flat view of a stent 10.
Figure 2B:
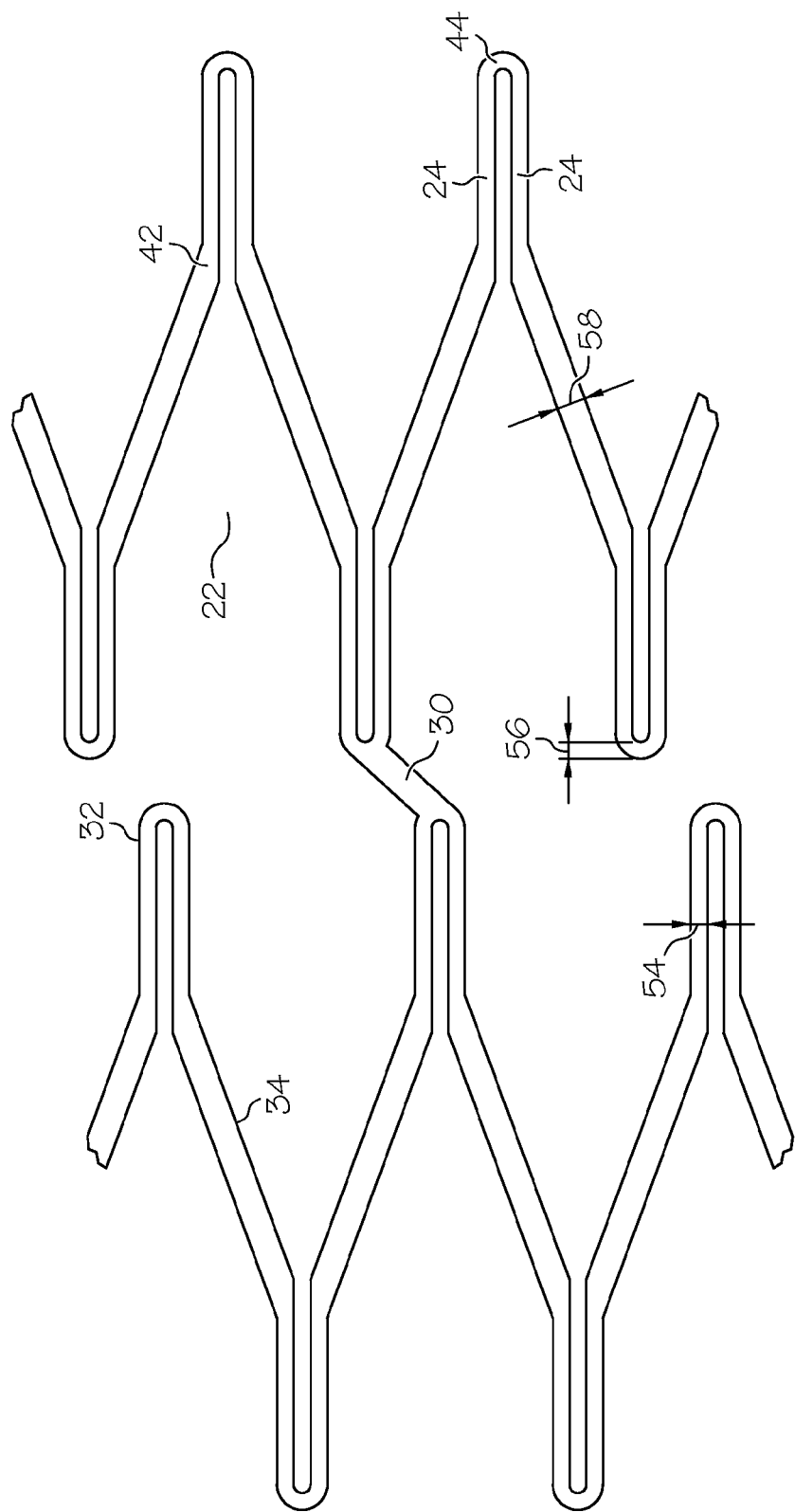
FIG. 2B detailed view of the stent of FIG. 2A.
Figure 2C:
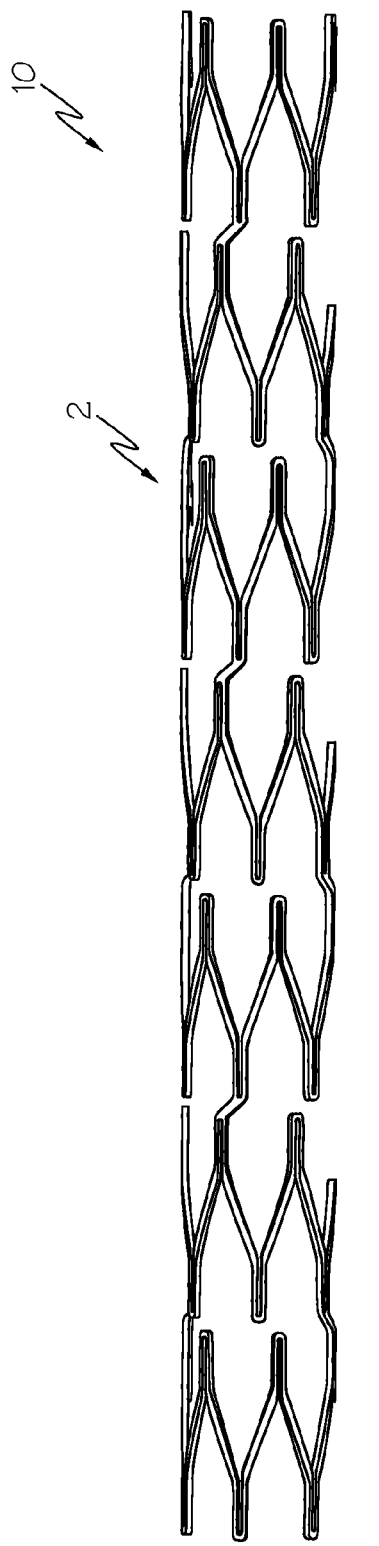
FIG. 2C is a side view showing ½ of the stent of FIG. 2A in an unexpanded configuration.

Turning to FIG. 2A, an embodiment of an expandable stent 10 is shown therein. The stent 10 of FIG. 2A is shown in the unexpanded configuration 2, prior to any expansion. The stent 10 has an unexpanded configuration 2, as shown in FIGS. 2A, 2B, and 2C, a nominally expanded configuration 4 (FIG. 2D), and a fully expanded configuration 6 (FIG. 2E).

The stent shown in FIGS. 2A-D can be distinguished from the stent shown in FIGS. 1A-D at least on the basis that, in the stent of FIGS. 2A-D, the bridges 32 do not extend into the openings 22. Instead, the bridges 32 of the stent of FIGS. 2A-D extend away from the respective openings 22.

Returning to FIG. 2A, the stent 10 comprises a plurality of circumferential bands 20 that extend circumferentially around the stent to form the stent wall. The bands 20 comprise a plurality of struts 34 and bridges 32 that connect circumferentially adjacent struts 34 to one another. In addition, the stent 10 comprises a plurality of connectors 30. The connectors 30 extend between longitudinally adjacent circumferential bands 20.

In some embodiments, the connectors 30 comprise a single straight segment that extends from a bridge 32 on one circumferential band 20 to an adjacent bridge 32 of the longitudinally adjacent circumferential band. In some embodiments, at least one of the connectors 30 extends both longitudinally and circumferentially, for example as shown in FIG. 2A. In some embodiments, the bridges 32 of longitudinally adjacent circumferential bands are offset from one another both longitudinally and circumferentially. Moreover, in some embodiments, the bridges 32 are circumferentially aligned with the bridges 32 of every-other band 20 such that the respective bridges lie on a common line of longitude.

In some embodiments, the connectors 30 are of any desirable length. Moreover, in some embodiments, the stent 10 does not include connectors between adjacent circumferential bands 20. In this regard, longitudinally adjacent circumferential bands 20 are directly connected one to another.

In some embodiments, the bridges 32 comprise two straight segments 24 connected to one another by a u-shaped segment 44. Each of straight segments 24 has a width 54 and each of the u-shaped segments 44 has a width 56. In some embodiments, the width 54 of one or more of the straight segments 24 is the same as the width 56 of the u-shaped segment 44. In some embodiments, the width 54 of one or more of the straight segments 24 is less than the width 56 of the u-shaped segment 44. Moreover, in some embodiments, the width 54 of one or more of the straight segments 24 is greater than the width 56 of the u-shaped segment 44. In this way, the stent 10 is configured to bend and deform in a desired manner, for example, with the u-shaped segments 44 bending prior to the straight segments 24, as the stent 10 is expanded.

In some embodiments, longitudinally adjacent circumferential bands are out-of-phase with one another. Moreover, in some embodiments, immediately adjacent circumferential bands are out-of-phase with one another by θ degrees (or radians).

The struts 34 have a width 58. In some embodiments, for example as shown in FIGS. 2A-2E, the strut width 58 does not change along the length of the strut 34. In some embodiments, however, the strut width 58 varies along the length of the strut 34.

Figure 2D:
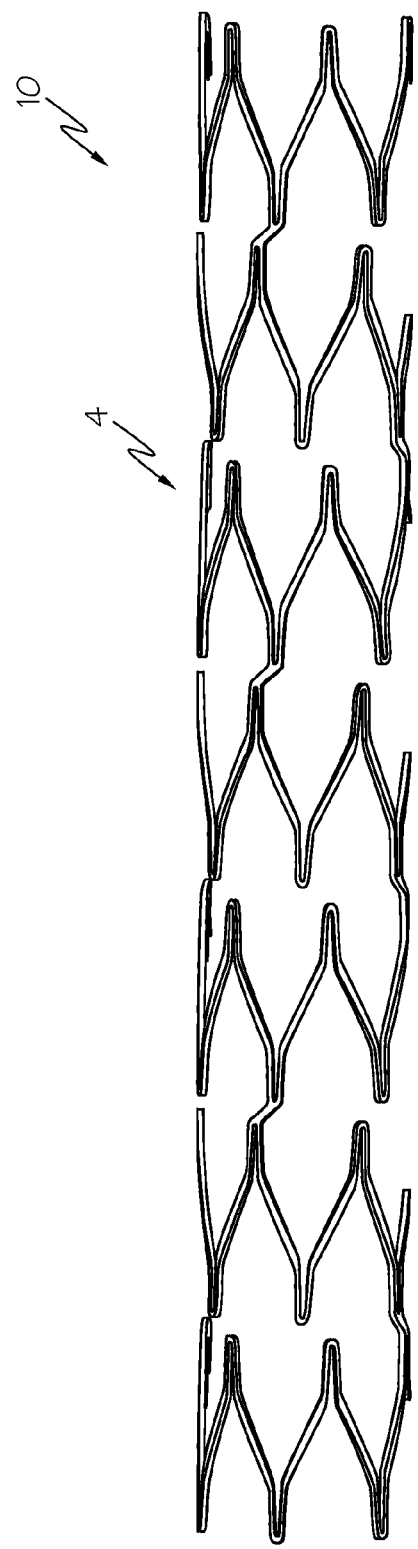
FIG. 2D is a side view showing ½ of the stent of FIG. 2A in a nominally expanded configuration.
Figure 2E:
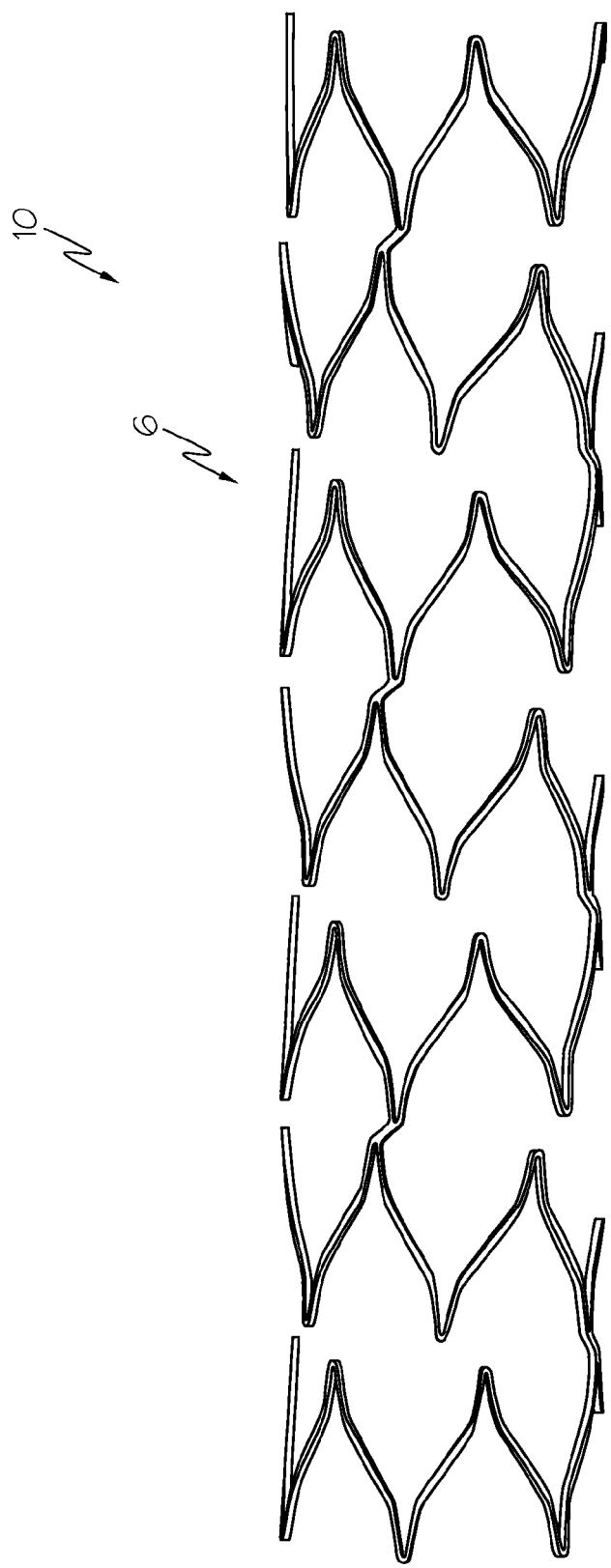
FIG. 2E is a side view showing ½ of the stent of FIG. 2A in a fully expanded configuration.

Turning to FIG. 2D, the stent 10 is shown in the nominally expanded configuration 4. In the nominally expanded configuration 4, in some embodiments, circumferentially adjacent straight segments 24 are deformed. In this regard, the straight segments 24 begin to flex prior to the struts 34, as the stent is expanded from the unexpanded configuration 2. Moreover, in some embodiments, the u-shaped segment 44 begins to flex prior to the struts 34.

As shown in FIG. 2E the stent 10 is expanded to the fully expanded configuration 6. In the fully expanded configuration 6, the straight segments 24 are further deformed. Moreover, in some embodiments, the stent 10 flexes at the u-shaped segment 44 first and then begins to flex at the intersection 42 of the straight segment 24 and the strut 34. In this way, the stent 10 expands in two stages, with the bridge deforming prior to the struts 34.

Figure 3A:
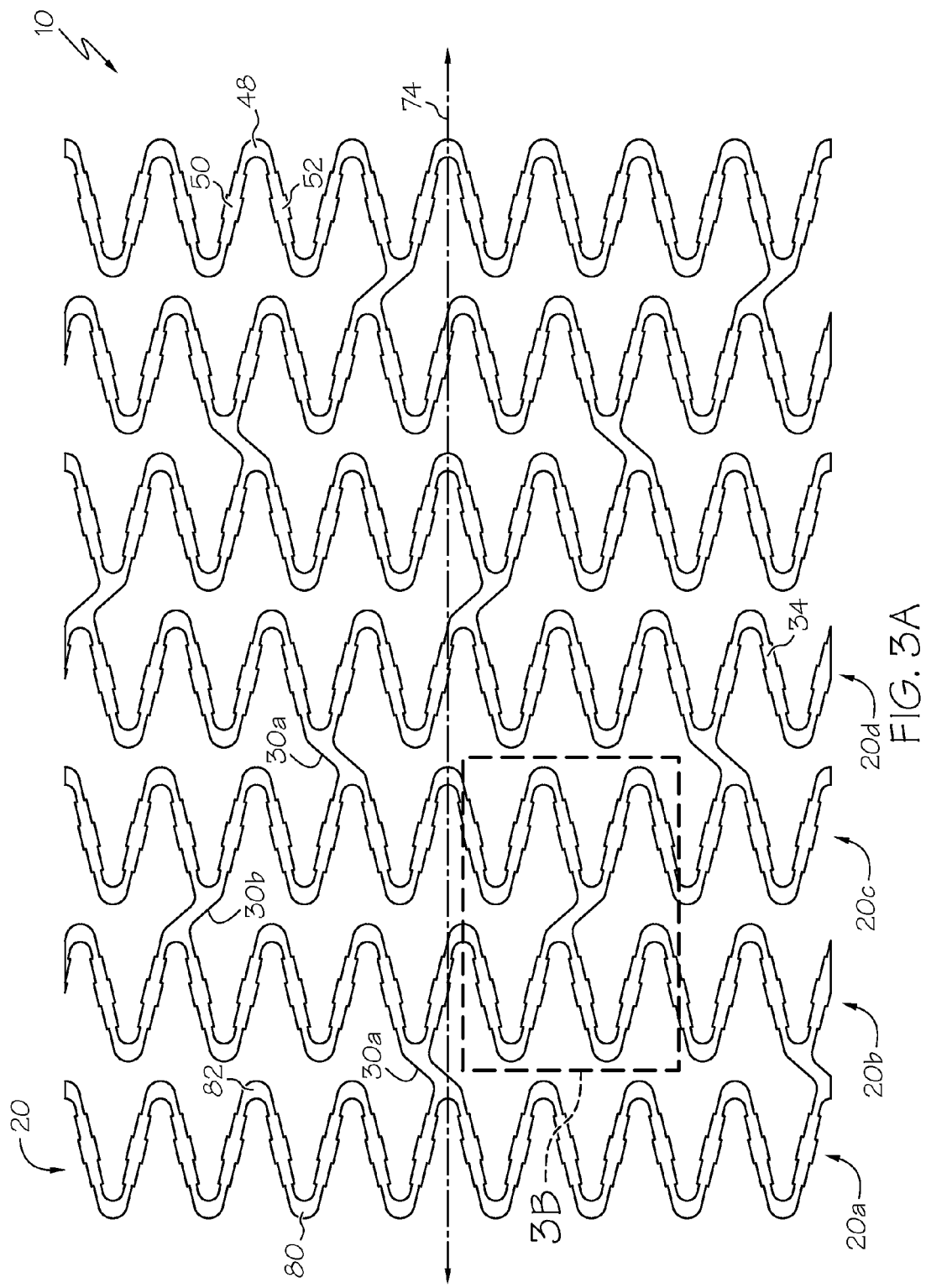
FIG. 3A is flat view of a stent 10.

With regard to FIG. 3A, a stent 10 is shown therein comprising a plurality of circumferential bands 20, each band having a serpentine shape. The bands 20 comprise strut pairs 48. Each of the strut pairs 48 of a circumferential band 20 comprises a plurality of struts 34. The struts 34 of the strut pairs 48 including a first strut 50 and a second strut 52. In some embodiments, the first strut 50 has a width that varies along the length of the strut 50. Also, in some embodiments, the second strut 52 has a width that varies along its length.

In some embodiments, the first strut 50 has a stepped-width, comprising a plurality of segments, each segment having a different width. Likewise, in some embodiments, the second strut 52 has a stepped-width, comprising a plurality of segments, each segment having a different width. In some embodiments, the first and/or second strut 50, 52 is wider at its middle than at one or both of its ends.

Figure 3B:
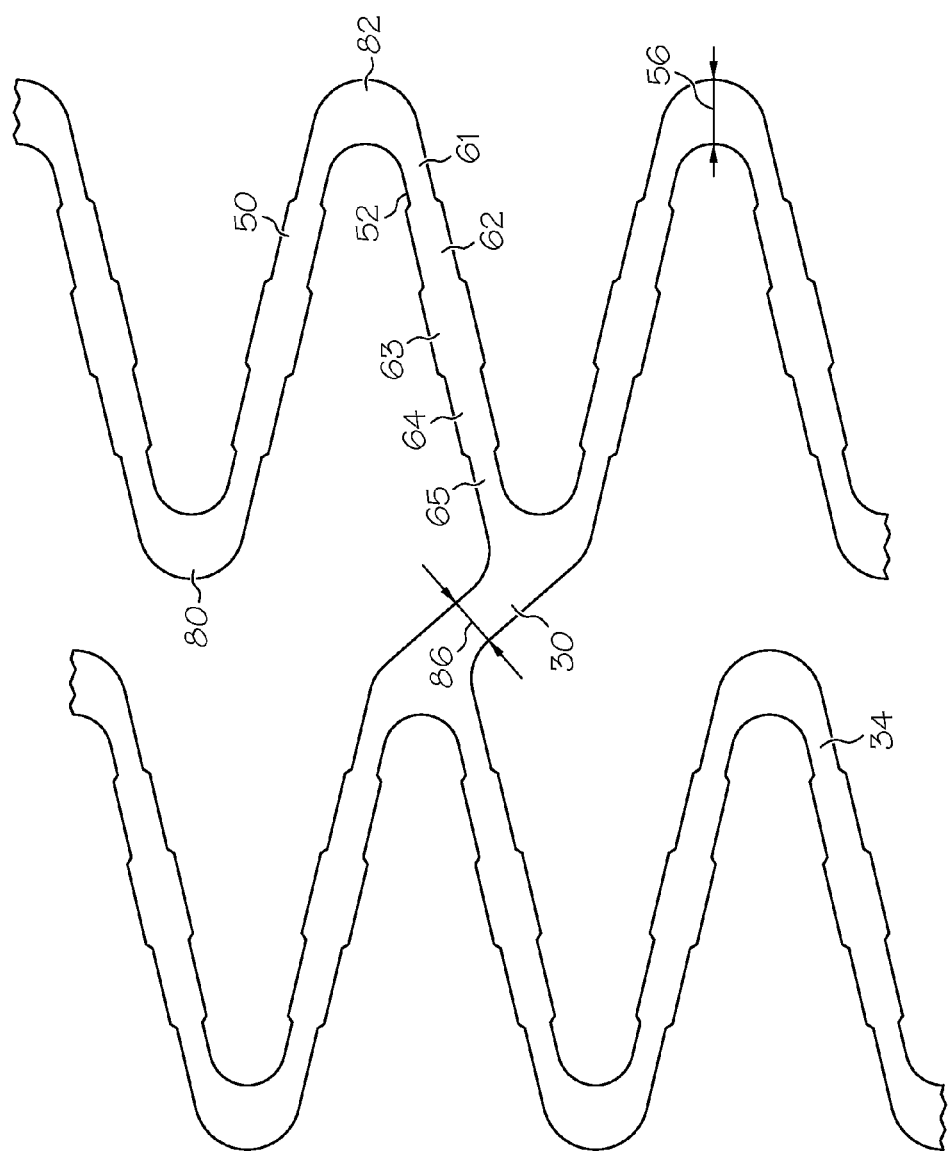
FIG. 3B detailed view of the stent of FIG. 3A.

As shown in greater detail in FIG. 3B, in some embodiments, each strut 50, 52 comprises five strut segments, including a first strut segment 61, a second strut segment 62, a third strut segment 63, a fourth strut segment 64, and a fifth strut segment 65. In some embodiments, the first and fifth strut segments 61, 65 have the same width as one another. And, in some embodiments, the second and fourth strut segments 62, 64 have the same width as one another. Moreover, in some embodiments, the width of the first and fifth strut segments 61, 65 is less than the width of the second and fourth strut segments 62, 64. In some embodiments, the width of the third strut segment 63 is greater than the width of the first, second, fourth, and fifth strut segments 61, 62, 64, 65. In some embodiments, the first and fifth strut segments 61, 65 are shorter than the second, third, and fourth strut segments 62, 63, 64.

In some embodiments, the bands 20 comprise proximal peaks 80 and distal valleys 82. The proximal peaks 80 alternate with the distal valleys 82 along a respective band 20. Moreover, in some embodiments, for example as shown in FIG. 3B, the proximal peaks 80 and distal valleys 82 have a width 56. In some embodiments, the width 56 of the proximal peaks 80 and/or distal valleys 82 is greater than the width of the remainder of the strut 34. In some embodiments, however, the proximal peaks and/or distal valleys are narrower than the remainder of the strut 34. And, in some embodiments, the width 56 of the proximal peaks and/or distal valleys 82 is greater than one or more of the segments 61, 62, 63, 64, 65 of one or more of the struts 34. In some embodiments, the widest part of the strut 34 is at its middle and the width of the peaks and valleys is greater than the strut segments 61-65.

In some embodiments, the stent 10 comprises a plurality of connectors 30 extending between and connecting longitudinally adjacent bands 20. In some embodiments, longitudinally adjacent bands 20 are connected to one another via two connectors 30. In some embodiments, the stent 10 comprises more than two connectors 30, for example 3-20 or more connectors. In some embodiments, the width 86 of the connectors 30 is less than the width 56 of the proximal peaks 80 and distal valleys 82. Moreover, in some embodiments, the width 86 of the connectors 30 is greater than one or more of the widths of the first, second, third, fourth, fifth, and sixth segments 61, 62, 63, 64, 65, respectively. In some embodiments, the width 86 of the connectors is greater than the width of the segments 61-65 but less than the width 56 of the proximal peaks 80 and distal valleys 82.

In some embodiments, the stent 10 comprises a plurality of circumferential bands 20 including a first band 20a, a second band 20b, a third band 20c, and a fourth band 20d. In some embodiments, the connectors 30a between the first band 20a and the second band 20b extend in a first direction. In some embodiments, the connectors 30b between the second band 20b and the third band 20c extend in a second direction which is different from the first direction. Moreover, in some embodiments, the connectors 30a between the third band 20c and the fourth band 20d extend in the first direction. In this way, the connectors 30 follow a repeating pattern, as shown in FIG. 3A, along the length of the stent 10.

In some embodiments, the proximal peaks 80 of the first band 20a are circumferentially offset from the proximal peaks 80 of the second band 20b. In addition, in some embodiments, the distal valleys 82 of the first band 20a are circumferentially offset from the distal valleys 82 of the second band 20b. In some embodiments, the proximal peaks 80 of first band 20a are circumferentially aligned with the proximal peaks 80 of the third band 20c such that the respective peaks lie on a common line of longitude as one another. Likewise, in some embodiments, the distal valleys 82 of the first and third bands 20a, 20c are circumferentially aligned. In some embodiments, the peaks and valleys, respectively, of every even band are circumferentially aligned. Further, in some embodiments, the peaks and valleys, respectively, of every odd band are circumferentially aligned.

Figure 3C:
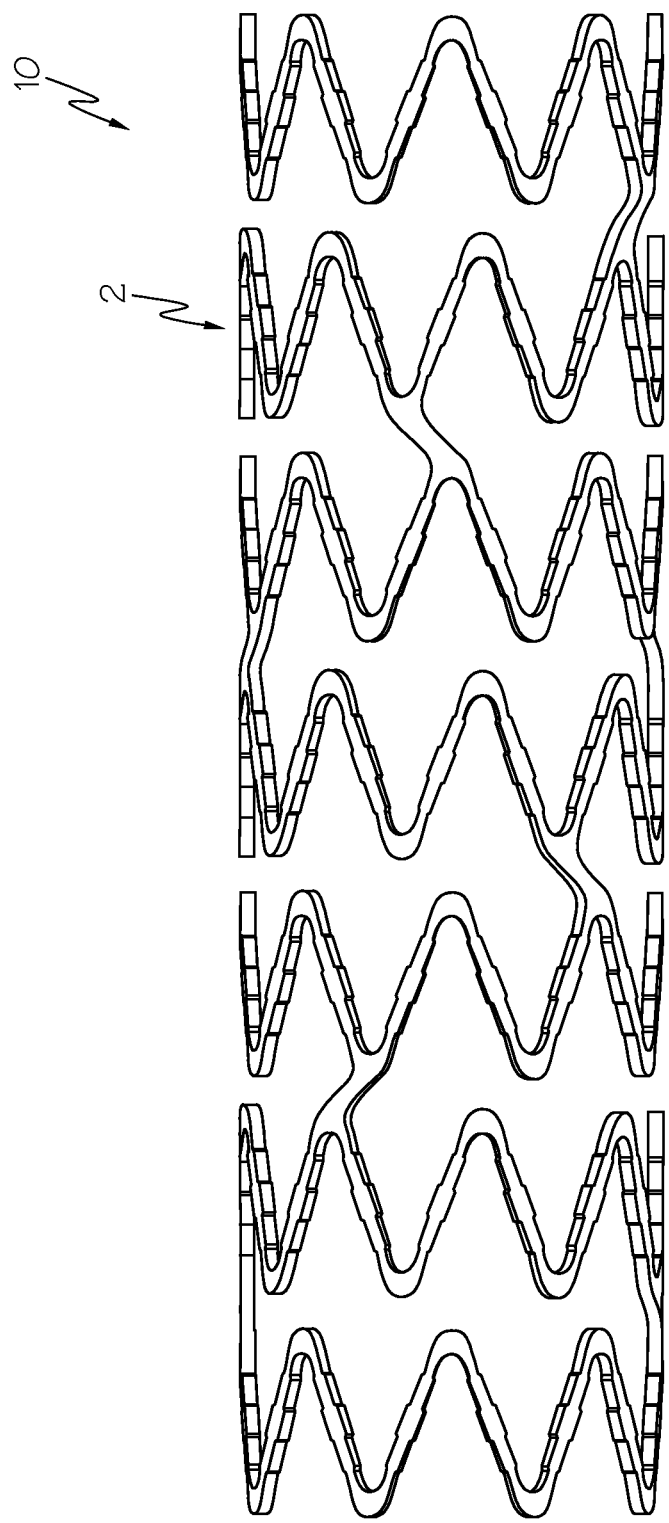
FIG. 3C is a side view showing ½ of the stent of FIG. 3A in an unexpanded configuration.
Figure 3D:
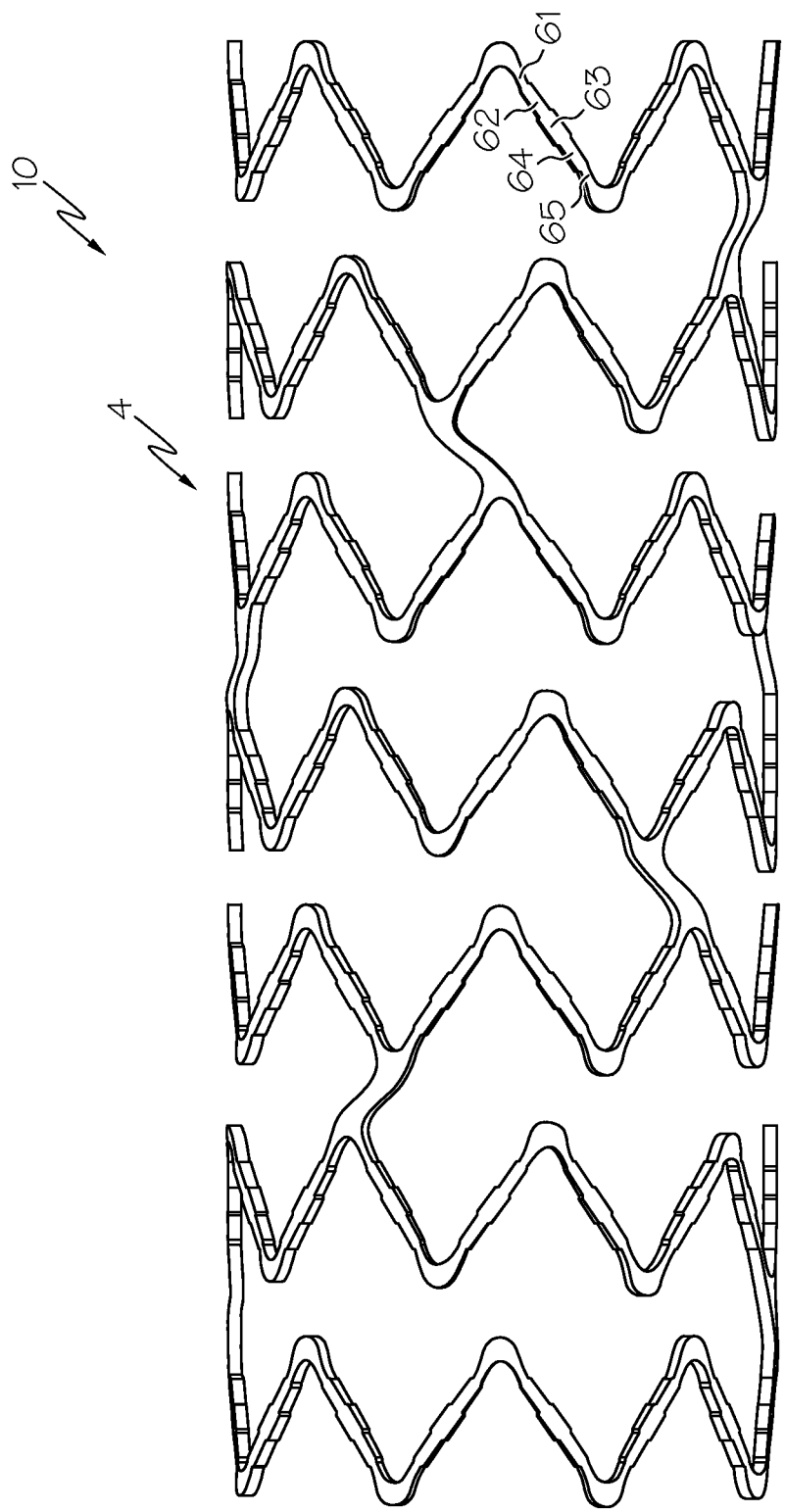
FIG. 3D is a side view showing ½ of the stent of FIG. 3A in a nominally expanded configuration.
Figure 3E:
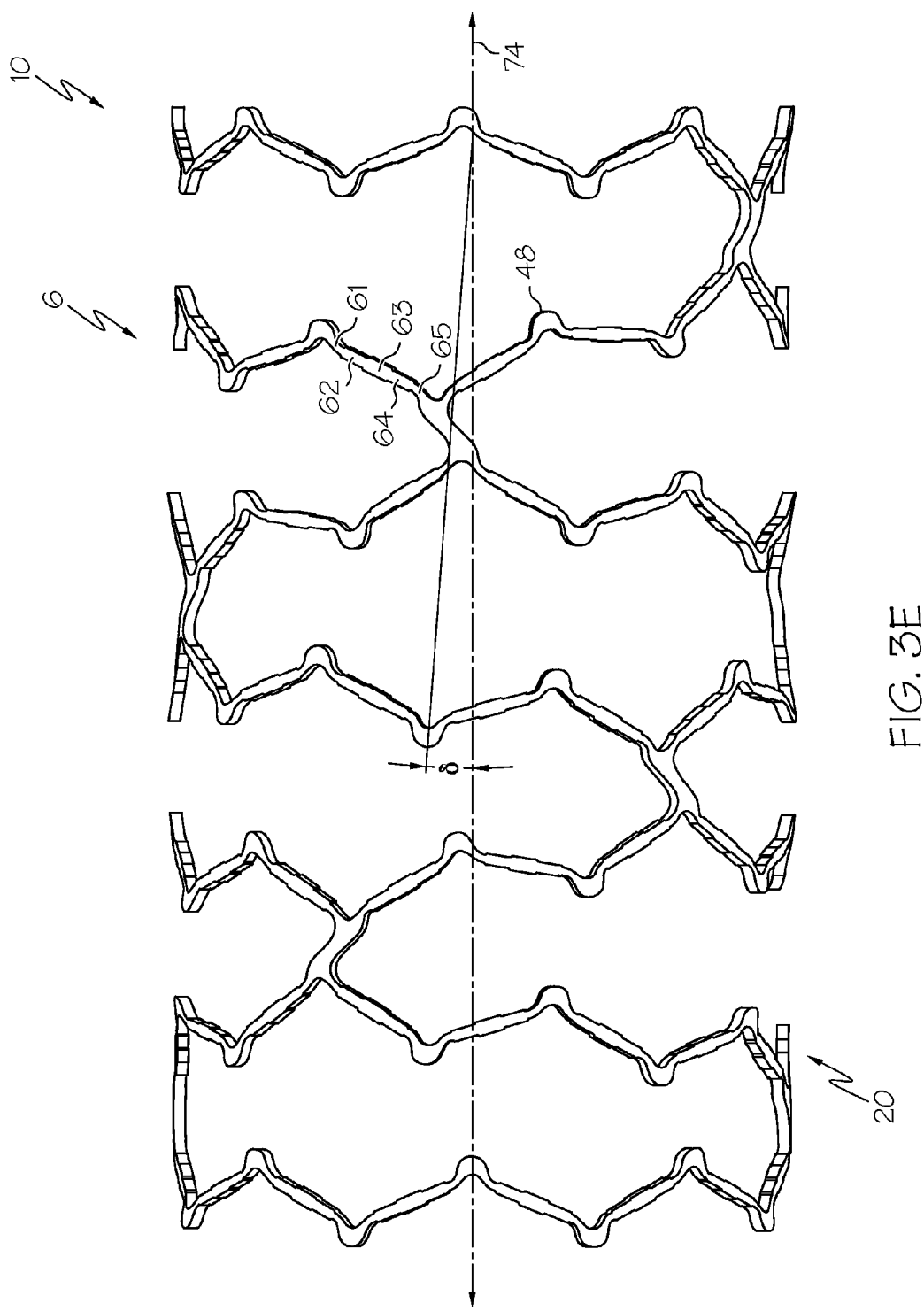
FIG. 3E is a side view showing ½ of the stent of FIG. 3A in a fully expanded configuration.

Turning to FIGS. 3C-3E, the stent 10 of FIGS. 3A, 3B is shown therein in three configurations—unexpanded (FIG. 3C), nominally expanded (FIG. 3D), and fully expanded (FIG. 3E). In the unexpanded configuration 2 of FIG. 3C, the stent 10 has not been deformed. In the nominally expanded configuration 4 of FIG. 3D, however, the stent 10 is deformed, with the first and fifth strut segments 61, 65, being weaker than the remainder of the strut segments 62-64.

In the fully expanded configuration 6 of FIG. 3E, the struts 34 are further deformed. In particular, in some embodiments, the first and fifth strut segments 61, 65 continue to deform. Moreover, the second and fourth strut segments 62, 64 begin to deform along their length.

As shown in FIG. 3E, in the fully expanded configuration 6, at least some of the strut pairs 48 are skewed relative to the longitudinal axis 74 by an angle δ. In this way, in some embodiments, upon expansion, at least some of the circumferential bands 20 have portions that are not orthogonal to the longitudinal axis 74 of the stent 10.

The inventive stents may be made from any suitable biocompatible materials including one or more polymers, one or more metals or combinations of polymer(s) and metal(s). Examples of suitable materials include biodegradable materials that are also biocompatible. In some embodiments, a stent can have one or more components constructed from one or more metals, polymers or combinations thereof that are corrodible so as to dissolve, dissociate, or otherwise break down in the body without ill effect. Examples of such materials have been referred to as being degradable, biodegradable, biologically degradable, erodable, bioabsorbable, bioresorbable, and the like. Biodegradable material will generally undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, platinum, chromium, gold, platinum-chromium alloys, and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol. Some further examples of biodegradable alloys, such as magnesium alloys and zinc alloys, are disclosed in U.S. Pat. No. 6,854,172 and U.S. 2006/0052864, the entire contents of which are hereby incorporated herein by reference.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

In addition to the foregoing, various features discussed or shown with respect to certain embodiments can be incorporated into other embodiments described herein or incorporated by reference. For example, the features described with respect to FIG. 1 are not limited to the embodiment of FIG. 1, and can be incorporated into embodiments shown, for example, in FIGS. 2 and 3.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent comprising:
an unexpanded configuration, a nominally expanded configuration, and an fully expanded configuration;
a plurality of longitudinally adjacent circumferential bands; and
a plurality of connectors;
in the unexpanded configuration, each circumferential band comprising:
a plurality of circumferentially adjacent strut pairs; and
a plurality of bridges, each strut pair comprising a first strut and a second strut, the first strut and the second strut being joined to one another by one of the bridges at a joined end, the first strut being angularly offset from the second strut by an acute angle; each bridge comprising two straight segments connected to one another by a u-shaped segment, the two straight segments being parallel to one another and angularly offset relative to the first and second struts, bridges extending into an opening defined by the first and second struts;
longitudinally adjacent circumferential bands being connected one to another by at least one of the connectors,
wherein the first and second struts are wider than the straight segments, and the bridges of longitudinally adjacent circumferential bands are circumferentially offset from one another; and
wherein a distance between the first strut and the second strut at the joined end is less than a distance between the first strut and the second strut at an unjoined end when the stent is in the nominally expanded configuration.

2. The stent of claim 1, wherein each connector further comprises a first end and a second end, the first end being longitudinally and circumferentially offset from the second end.

3. The stent of claim 1, wherein the plurality of longitudinally adjacent circumferential bands comprises odd bands and even bands, bridges of the odd bands being aligned with one another on a common line of longitude and bridges of the even bands being aligned with one another on a common line of longitude; the bridges of the even bands being unaligned with the bridges of the odd bands.

4. The stent of claim 1, wherein, in the nominally expanded configuration, the bridges of the stent are elastically deformed and the struts remain straight.

5. The stent of claim 1, wherein, in the fully expanded configuration, the bridges of the stent are elastically deformed and the struts are elastically deformed.

6. The stent of claim 1, wherein at least one of the bands has two connectors extending proximally therefrom and two connectors extending distally therefrom.

7. The stent of claim 6, wherein a plurality of the bands have six distally extending bridges and six proximally extending bridges.

8. The stent of claim 1, wherein the connectors comprise first connectors and second connectors, the first connectors being non-parallel relative to the second connectors.

9. The stent of claim 8, wherein the first connectors extend proximally from odd bands to even bands and the second connectors extend proximally from even bands to odd bands.

10. A stent comprising:
an unexpanded configuration, a nominally expanded configuration, and a fully expanded configuration;
a plurality of circumferential bands and a plurality of connectors connecting adjacent circumferential bands to one another;
each circumferential band comprising:
a plurality of struts interconnected by bridges, adjacent struts forming strut pairs and being connected to one another at a first end or a second end but not both, each strut pair defining an opening therebetween, the bridges extending into the openings, wherein circumferentially adjacent ends of adjacent struts of a respective strut pair are closer to one another when the stent is in the nominally expanded configuration than when the stent is in the unexpanded configuration;
in the unexpanded configuration:
the struts being straight along their length, and the bridges comprising two adjacent straight segments connected by a u-shaped segment, the straight segments being parallel to one another and to the longitudinal axis of the stent.

11. The stent of claim 10, wherein circumferentially adjacent ends of adjacent struts of a respective strut pair are closer to one another when the stent is in the nominally expanded configuration than when the stent is in the fully expanded configuration.

12. The stent of claim 10, wherein circumferentially adjacent ends of adjacent struts of a respective strut pair are closer to one another when the stent is in the unexpanded configuration than when the stent is in the fully expanded configuration.

13. The stent of claim 10, wherein the struts have a strut width and each of the straight segments has a segment width, the strut width being greater than the segment width.

14. The stent of claim 10, wherein each connector further comprises a first end and a second end, the first end being longitudinally and circumferentially offset from the second end.

15. The stent of claim 10, wherein the connectors have a connector width and each of the straight segments has a segment width, the connector width being greater than the segment width.

16. The stent of claim 10, wherein the strut pairs of each circumferential band comprises distal valleys and proximal peaks, the connectors extending from a distal valley of one band to a proximal peak of a longitudinally adjacent circumferential band.

17. The stent of claim 10, wherein the plurality of circumferential bands comprises odd bands and even bands, bridges of the odd bands being aligned with one another on a common line of longitude and bridges of the even bands being aligned with one another on a common line of longitude; the bridges of the even bands being unaligned with the bridges of the odd bands.

18. A stent having an unexpanded configuration and a nominally expanded configuration, the stent comprising:
- a plurality of circumferential bands and a plurality of connectors connecting adjacent circumferential bands to one another;
- each circumferential band comprising:
  - a plurality of struts interconnected by bridges, adjacent struts forming strut pairs and being connected to one another at a first end or a second end but not both, each strut pair defining an opening therebetween, the bridges extending into the openings, wherein circumferentially adjacent ends of adjacent struts of a respective strut pair are closer to one another when the stent is in the nominally expanded configuration than when the stent is in the unexpanded configuration;
- in the unexpanded configuration:
  - the struts being straight along their length, and the bridges comprising two adjacent straight segments connected by a u-shaped segment, the straight segments being parallel to one another and to the longitudinal axis of the stent.

* * * * *